United States Patent [19]

Preidel

[11] Patent Number: 5,562,815

[45] Date of Patent: Oct. 8, 1996

[54] APPARATUS AND METHOD FOR THE ELECTROCHEMICAL DETERMINATION OF THE OXYGEN CONCENTRATION OF A LIQUID MEDIUM

[75] Inventor: Walter Preidel, Erlangen, Germany

[73] Assignee: Pacesetter AB, Solna, Sweden

[21] Appl. No.: 385,701

[22] Filed: Feb. 8, 1995

[30] Foreign Application Priority Data

Feb. 9, 1994 [DE] Germany ............................ 44 04 130.6

[51] Int. Cl.$^6$ ............................................. G01N 27/26
[52] U.S. Cl. .................... 205/782; 204/400; 204/412; 204/415; 205/775; 205/786
[58] Field of Search ........................ 204/400, 415, 204/431; 205/775, 782, 782.5, 783

[56] References Cited

U.S. PATENT DOCUMENTS

| | | | |
|---|---|---|---|
| 2,913,386 | 11/1959 | Clark, Jr. | 204/415 |
| 3,260,659 | 7/1966 | Willing et al. | 205/717 |
| 4,075,596 | 2/1978 | Plasko | 337/408 |
| 4,853,091 | 8/1989 | Mund et al. | 204/402 |
| 5,225,063 | 7/1993 | Gumbrecht et al. | 204/402 |
| 5,376,244 | 12/1994 | Preidel | 205/786 |

FOREIGN PATENT DOCUMENTS

| | | |
|---|---|---|
| 170998 | 2/1986 | European Pat. Off. . |
| 4014109 | 11/1991 | Germany . |

*Primary Examiner*—T. Tung
*Attorney, Agent, or Firm*—Hill, Steadman & Simpson

[57] ABSTRACT

An apparatus and method of electrochemically determining an oxygen concentration with an oxygen sensor that includes a working electrode. The working electrode has a potential profile that includes a first potential step (a first measuring potential), a second potential step (a second measuring potential) and a third potential step. A measuring period is provided at the first and second measuring potentials. The currents flowing at the first and second measuring potentials are calculated and integrated over time. One of the two measuring potentials may be varied, depending on the difference between the two integrals of the currents flowing at the first and second measuring potentials, until the two integrals equal 0. An oxygen concentration is then determined from the value of a potential which thereby results.

20 Claims, No Drawings

APPARATUS AND METHOD FOR THE ELECTROCHEMICAL DETERMINATION OF THE OXYGEN CONCENTRATION OF A LIQUID MEDIUM

BACKGROUND OF THE INVENTION

The present invention relates to a method for the electrochemical determination of the oxygen concentration with an oxygen sensor that comprises a working electrode.

The measurement of the partial oxygen pressure is an important analytical problem. A rapid and exact calculation of the oxygen value is necessary, particularly in medical technology. The determination of the oxygen in the blood of patients, for example, requires a precision of approximately 1 Torr, namely in the range between about 10 and 300 Torr. The drift of the signal should thereby not exceed a value of 5 Torr over the course of three days, this essentially corresponding to the duration of the measurement in the blood. Heretofore, oxygen sensors employed in medical technology, however, fall far short of satisfying these demands.

The oxygen sensor of Clark is currently still being generally utilized in medical technology (in this respect, see U.S. Pat. Nos. 2,913,386; 3,260,659 and 4,075,596). Although this sensor can, in fact, be employed in blood gas analyzers, it is not suitable for identifying the oxygen content in the blood, since an implantation or, respectively, a longer-lasting operation in the body is prevented by some critical sensor features. Included among them, for example, is a hydrophobic membrane that is arranged in front of the measuring electrode. The properties of this hydrophobic membrane are noticeably modified due to interactions in the body. Moreover, the constant and high oxygen consumption of the sensor leads to a pronounced rejection reaction that makes operation of the sensor even more difficult.

European Published Application 0 170 998 discloses a method for the electrochemical determination of the oxygen concentration, particularly in biological material, with an oxygen sensor that comprises a measuring electrode and a cooperating electrode. In this method, the measuring electrode has two potentials cyclically impressed on it and the current flowing during the measuring phase is interpreted as measured signal. The method mainly serves the purpose of measuring relative changes in the oxygen concentration in order to match the frequency of a heart pacemaker to the patient's requirements.

Given employment of oxygen sensors in intensive care, it is necessary to exactly identify the partial oxygen pressure, with optimally little drift, over a time span of several days. A method disclosed by German Published Application 40 14 109 is suitable for this purpose. In this method, the measuring or, respectively, sensor electrode (of the oxygen sensor) has a potential profile impressed on it having a plurality of potential steps, namely two measuring potentials and a quiescent potential. At a measuring potential, the current is thereby integrated in the potential range of the oxygen reduction; the other measuring potential lies above the reduction potential of oxygen, so that the current only covers the reactions occurring at the electrode. A signal for the partial oxygen pressure that is suitable for calibration is then obtained by forming the difference between the two integrals.

Measurements in vitro and in vivo in the blood have shown that the conventional method is not yet precise enough and low-drift enough for the required precision of only a few Torr deviation. Added thereto is that various electrodes have surfaces that differ in size, even given mass production, and, thus, have variable activity such that the measuring error can proceed beyond the required maximum error (in the oxygen pressure) of a few Torr.

SUMMARY OF THE INVENTION

An object of the present invention is to provide a method and an apparatus for the electrochemical determination of the oxygen concentration, with an oxygen sensor comprising a working electrode, that delivers a comparable measured signal despite different electrode areas under the same ambient conditions.

This object is achieved by a working electrode having a potential profile with a plurality of potential steps impressed upon it. A first potential step lies in the range between −700 and −1000 mV (a first measuring potential). A second potential step lies in the range between −750 and −1100 mV (a second measuring potential). A third potential step lies in the range between +150 and −300 mV. Each measuring potential is, respectively, referred to an Ag/AgCl reference electrode.

The dwell time at the two measuring potentials, respectively, amounts to between 10 and 100 measuring period (ms). The current flowing at the two measuring potentials is identified and is respectively integrated over time, whereby the integration respectively begins 5–35 ms after the beginning of the measuring period and lasts between 5 ms and 35 ms.

One of the two measuring potentials is modified depending on the difference between the two integrals ($\Delta Q$) until $\Delta Q=0$. The oxygen concentration is calculated from the value of the potential that thereby results.

Other advantages and features of the invention will be readily apparent from the description of the presently preferred embodiments and claims.

DESCRIPTION OF THE PREFERRED EMBODIMENTS

Pursuant to the present invention, a method is provided for the electrochemical determination of the oxygen concentration. In this method, the integrals of the current are calculated at the two measuring potentials. One of the two measuring potentials is slightly raised or lowered, based on the value of the difference between these two integrals and the operational sign of the difference, namely until the two integrals are the same, i.e., the difference between the integrals $\Delta Q$ is 0. The other measuring potential thereby remains unmodified. When $\Delta Q$ is greater than 0, either the first measuring potential is lowered or the second measuring potential is raised. If $\Delta Q$ is less than 0, the first measuring potential is raised or the second measuring potential is lowered. The potential obtained in this way is then the measured value. The difference between this potential and the invariable measured potential is a criterion of the partial oxygen pressure (in the electrolyte).

The present invention is suitable, for example, for identifying the oxygen concentration in body fluids; however, it can also be advantageously employed for calibrating oxygen electrodes. The reduction current of oxygen is area-proportional at low measuring potentials, for example, −1 V as compared to an Ag/AgCl anode. Since the activity of the electrode material cannot be adequately reproduced, this is inadequate for a calibration of sensors. Further information about the sensor, by contrast, is required for this purpose. The method of the present invention, however, is largely independent of the electrode area and, thus, does not deliver an area-proportional signal because influences due to the electrode area and differences in activity are suppressed. It is, therefore, especially well-suited for calibrating oxygen electrodes.

In addition, there is also the possibility of identifying the capacitance of the working electrode on the basis of an impedance measurement undertaken while impressing an unstepped potential on the working electrode. A correction quantity, to which the integral of the non-varied potential is referred, is obtained in this way, i.e., the quotient of the value of this integral and the value of the capacitance measurement is formed. A second measured quantity that can serve the purpose of correcting the actual measured value is obtained in this way.

The potential profile that is generally impressed on the working electrode (measuring electrode, sensor electrode) with a potentiostat is composed of three potential steps. The first step lies in the potential range of about −700 through −1000 mV, preferably at approximately −800 mV. The second step lies in the range of about −750 through −1100 mV, preferably at approximately −1000 mV. The third step lies in the range of about +150 through −300 mV, preferably at approximately 0 mV. At this potential, which represents the quiescent phase of the working electrode, only an extremely slight current still flows after the phase of the charge reversal of the double-layer capacitance (of the working electrode). After the charge reversal, approximately 5 ms through 20 ms thereafter, the potentiostat can therefore be switched off, for example, with an analog switch. However, it is also possible to already shut the potentiostat off at the end of the second potential step and to allow the electrode to float in terms of its potential until the next loading. A potential of approximately −250 mV then occurs after approximately 10 ms through 200 ms. The shut-off of the potentiostat saves energy. Therefore, this procedure is especially suitable for fully implanted sensors.

The dwell time at the two measuring potentials, respectively, amounts to between approximately 10 and 100 ms, advantageously between approximately 10 and 40 ms and, preferably, to about 20 ms. The dwell time at the third potential step, i.e., the quiescent phase of the working electrode, advantageously amounts to between approximately 0.5 and 10 s, and, preferably, to about 2 s. The total time of a measuring event preferably lies in the range of about 1.5 through 5 s.

The integration of the current at the measuring potentials starts approximately 5 through 35 ms after the beginning of the measuring period, and, preferably, after about 15 ms. The integration itself respectively lasts between approximately 5 and 35 ms, and, preferably, at about 5 ms. Advantageously, the dwell time and/or the beginning of the integration and/or the duration of the integration is the same at the two measuring potentials.

Pursuant to the present invention, an apparatus is provided for the electrochemical determination of the oxygen concentration with an oxygen sensor that employs a working electrode. The working electrode has a potential profile including a plurality of potential steps impressed on the potential profile.

The first potential step is implemented at −800 mV with a duration of 20 ms; the second potential step is implemented at −1000 mV with a duration of 20 ms; and the third potential step is implemented at 0 mV with a duration of 1960 ms.

The current is measured during the first two potential steps and the integral is respectively formed for the duration of 5 ms, 15 ms after the beginning of the measuring period.

The oxygen sensor utilized in the method and apparatus of the present invention is constructed in a known way. A flow-through measuring cell or a rod-shaped sensor or, respectively, a catheter sensor for immersion into the electrolyte is employed for general applications. An invasive or, respectively, implantable version, having a catheter-shaped structure of a planar embodiment that is attached to the surface of other implants or of housings and other arrangements that is in contact with blood, tissue fluid, tissue or an organ is employed for medical applications.

The sensor generally comprises the classic three-electrode arrangement having a working electrode, a reference electrode and a cooperating electrode. It is possible to combine the reference electrode with the cooperating electrode to form a single electrode if the potential of this electrode under load is stable enough for measurement. Vitreous carbon, pyrographite or some other carbon material having low electro-catalytic activity and a low double-layer capacitance serves as material for the working electrode. The reference electrode is an Ag/AgCl electrode or a similarly potential-stable electrode. The cooperating electrode is composed of a material such as platinum, gold, titanium, stainless steel, carbon, activated vitreous carbon, pyrographite or activated pyrographite.

Although various minor modifications may be suggested by those versed in the art, it should be understood that I wish to embody within the scope of the patent granted hereon all such modifications as reasonably and properly come within the scope of my contribution to the art.

I claim:

1. An apparatus for electrochemically determining an oxygen concentration in a liquid medium with an oxygen sensor comprising:

a working electrode disposed for interacting with said liquid medium;

means for impressing a plurality of potential steps upon the working electrode including a first potential step of a first measuring potential in a range of −700 mV to −1000 mV, a second potential step of a second measuring potential in a range of −750 mV to −1100 mV, and a third potential step of a measuring potential in a range of +150 mV to −300 mV, with a measuring period at the first potential step and the second potential step in a range of 10 ms and 100 ms;

means for calculating a current flow at the first potential step and second potential step by integrating the current flow over time, beginning at a time in a range of 5 ms to 35 ms after a starting time of the measuring period and having a duration in a range of 5 ms to 35 ms, to obtain a first integral at the first measuring potential and a second integral at the second potential;

means for determining a difference between the first integral and the second integral and for varying at least one of the measuring potentials until reaching a final potential at which the difference between the first integral and the second integral equals 0, said means for impressing comprising means for impressing said final potential upon said working electrode; and means for determining the oxygen concentration of said liquid medium with said working electrode at said final potential.

2. The apparatus of claim 1, further comprising means for bringing a flow of blood into contact with said working electrode as the liquid medium.

3. The apparatus of claim 1, wherein said means for impressing includes an Ag/AgCl reference electrode relative to which said potential steps are referenced and wherein the third potential step is a floating reference voltage produced by said Ag/AgCl reference electrode.

4. The apparatus of claim 1, wherein said means for impressing comprises means for impressing the first potential step at approximately −800 mV, the second potential step at approximately −1000 mV and the third potential step at approximately 0 mV.

5. The apparatus of claim 1, wherein the means for calculating comprises means for integrating the current flow at each of the first potential step and the second potential step for a measuring period in a range of 10 ms to 40 ms.

6. The apparatus of claim 1, wherein the means for calculating comprises means for integrating the current flow at each of the first potential step and the second potential step for approximately 20 ms.

7. The apparatus of claim 1, wherein the means for impressing comprises means for impressing said first and second measuring potentials for a measuring period, and the means for calculating comprises means for integrating the current flow at said first and second measuring potentials for a duration and starting time, which are all the same for the first potential step and the second potential step.

8. The apparatus of claim 1, wherein the means for impressing comprises means for impressing said potential in said third potential step for a measuring period in a range of 0.5 s to 10 s.

9. The apparatus of claim 1, wherein the means for impressing comprises means for impressing said potential in said third potential step for a measuring period of approximately 2 s.

10. The apparatus of claim 1, wherein said means for impressing comprises means for impressing an unstepped potential on said working electrode, wherein said apparatus further comprises impedance measuring means for measuring a capacitance of said working electrode with said unstepped potential impressed thereon, wherein said means for calculating comprises means for integrating said current flow for a time with said unstepped potential impressed on said working electrode to obtain a correction integral and for dividing said correction integral by said capacitance to obtain a correction factor and for correcting at least one of said first and second integrals with said correction factor.

11. A method for the electrochemical determination of an oxygen concentration of a liquid medium with an oxygen sensor that includes a working electrode comprising the steps of:

impressing a potential profile having plurality of potential steps on the working electrode including a first potential step at a first measuring potential, a second potential step at a second measuring potential, and a third potential step at a potential;

impressing the first measuring potential and the second measuring potential for a measuring period;

conducting an integration of current flow beginning after a start of the measuring period over an integration duration;

during said integration duration, integrating a first current flowing at the first measuring potential to obtain a first integral and integrating a second current flowing at the second measuring potential to obtain a second integral;

varying one of said first and second measuring potentials dependent upon a difference between the first integral and the second integral until the difference between the first integral and the second integral equal 0 to identify a final potential at which said difference is 0; and impressing said final potential on said working electrode and determining the oxygen concentration of the liquid medium with said final potential impressed on said working electrode.

12. The method of claim 11, further comprising the step of impressing the first potential step in a range of −700 mV to −1000 mV, the second potential step in a range of −750 mV to −1100 mV, and the third potential step in a range of +150 mV to −300 mV.

13. The method of claim 11, further comprising the step of impressing the first potential step at approximately −800 mV, the second potential step at approximately −1000 mV and the third potential step at approximately 0 mV.

14. The method of claim 11, further comprising the step of integrating the first current flowing at the first measuring potential and the second current flowing at the second measuring potential for the measuring period in a range of 10 ms to 100 ms.

15. The method of claim 11, further comprising the step of impressing the first measuring potential and the second measuring potential for a measuring period in a range of 10 ms to 40 ms.

16. The method of claim 11, further comprising the step of impressing the first measuring potential and the second measuring potential for a measuring period of approximately 20 ms.

17. The method of claim 11, further comprising the step of integrating the first current flowing at the first measuring potential and the second current flowing at the second measuring potential for the start of the measuring period and the integration duration, which are the same for the first measuring potential and the second measuring potential.

18. The method of claim 11, further comprising the step of impressing a potential in the third potential step for a measuring period in a range of 0.5 s to 10 s.

19. The method of claim 11, further comprising the step of impressing a potential in the third potential step for a measuring period of approximately 2 s.

20. The method of claim 11, further comprising the steps of:

impressing an unstepped potential on said working electrode;

measuring a capacitance of the working electrode through an impedance measurement with said unstepped potential impressed thereon;

obtaining a correction integral by integrating said current flow over a time with said unstepped potential impressed on said working electrode;

dividing the correction integral by the capacitance to obtain a correction factor; and correcting at least one of the first and second integrals with the correction factor.

* * * * *